United States Patent [19]

Marsland

[11] Plant 4,900

[45] Oct. 26, 1982

[54] APPLE TREE

[76] Inventor: William P. Marsland, Rte. 3, Box 166, Spring Hill, Kans. 66083

[21] Appl. No.: 197,640

[22] Filed: Oct. 16, 1980

[51] Int. Cl.[3] ..... A01H 5/00
[52] U.S. Cl. ..... Plt./34
[58] Field of Search ..... Plt./34

*Primary Examiner*—James R. Feyrer
*Attorney, Agent, or Firm*—Frank B. Robb

[57] ABSTRACT

An apple tree which is more open growing with wider crotch angles, developing a heavy fruit spur system throughout the entire tree, fruit production tending to commence on the previous year's growth rather than older wood, this characteristic being especially true in young trees, thus emphasizing open growing, the fruit exhibiting a full bright red color, less prominent dots, and much more waxy skin texture that resists cracking, than the usual and known Stayman apple trees.

1 Drawing Figure

The present invention relates to a new and distinct variety of apple tree which was discovered by me as a limb sport of the commonly known Stayman variety (unpatented) and which I have chosen to call Genesis II.

My discovery was made in my cultivated orchard located at Spring Hill, Kans. At the time of my discovery and while engaged in the routine care of the orchard, my attention was attracted to one tree having fruit which appeared to be distinctly different from the fruit on other limbs of that tree and on other trees of the same variety growing nearby.

Close and prolonged observation of this particular tree convinced me that the limbs bearing the unusual fruit was the result of a bud sport and I thereupon took prompt steps to preserve the limbs and to keep them under close observation.

I have asexually reproduced the new sport by budding and grafting. The progeny resulting and continued observation and tests of the original limb sport on the parent tree over a period of years have established that the sport is definitely a new and distinct variety as particularly evidenced by the following unique characteristics which are outstanding and which distinguish the sport from the standard Stayman apple as well as other varieties of which I am aware.

1. A general resemblance of the fruit to the fruit of the Stayman apple variety but having a much earlier habit of fruit coloring and maturing at Spring Hill, Kans. with a full bright red color about 5–10 days earlier than the standard Stayman apple.
2. The color of the fruit appears to have a bright red blush with less prominent dots as contrasted with the dull red color, prominent dots and stripe of the standard Stayman apple.
3. A fruit having skin that is of a more waxy texture than the standard variety.
4. A substantial overall red color effect over about 50% of the apple and usually over about 75% of the apple with the remaining ground coloring being a light green to yellow color depending on maturity.
5. A general resemblance of the tree to the parent variety but producing a smaller tree overall.
6. A more open growing tree with wider crotch angles.
7. A much heavier fruit spur system throughout the tree.
8. A habit of beginning the production of fruit on previous year's growth rather than on older wood which is common with most other apple varieties. This propensity to fruit on one year old wood is particularly evident in young trees which results in the open growing characteristics and dwarfing effects on the tree. In older trees this propensity to fruit on one year old wood is less dramatic and usually manifests itself as a secondary bloom on one year old wood after the primary bloom occurs on older wood.

The accompanying drawing shows typical specimens of the foliage as borne on a typical branch section, as well as typical specimens of the fruit, one of the fruit specimens being shown in cross-section, all as depicted in color as nearly true as it is reasonably possible to make the same in a color illustration of this character.

The following is a detailed description of my new variety, with color terminology in accordance with Munsell Limit Color Cascade (hereinafter abbreviated as (M), except where general color terms of ordinary dictionary significance are suitable. Detailed description of the tree and fruit follows:

Locality where grown and observed: Spring Hill, Kans.

Dates of first and last pickings: About Sept. 29–Oct. 6.

Tree: Medium size, vigorous, spreading, rapid growing with wide crotch angles, non-brittle wood, hardy, productive, regular bearer. Tree is smaller and more open than standard Stayman.

Trunk: Similar to parent variety.

Branches: Medium, resilient, wide angle crotches. Tips tend to weep on older trees resulting from fruit loads. A heavier fruit spur system than the standard Stayman, especially on one year old wood.

Lenticles: Similar to standard Stayman.

Leaves: Large, similar to standard Stayman in order, color, shape, but placed at shorter internodal distances.

Flowers: Large white with prominent pink borders and/or stripes 42-3 (M). Variety shows slightly more pink than standard Stayman.

Dates of first and full bloom: About Apr. 26 and about May 2. First bloom somewhat later than standard Stayman.

Fruit:

*Maturity when described.*—Eating ripe Oct. 7.

*Size.*—Uniform, axial diameter — about 2½". Transverse diameter — about 3".

*Form.*—Round conical. Less conical than standard Stayman.

*Cavity.*—Symmetrical; depth about $\frac{5}{8}''$. Breadth about $1\frac{3}{8}''$ with fine russet, 23-8 (M). Sometimes resembles cavity of the Rome Beauty apple (unpatented).

*Basin.*—Symmetrical; depth about $\frac{1}{4}''$. Breadth about $1\frac{1}{4}''$. Usually deeper and more pronounced than standard Stayman.

*Stem.*—Clubbed; stout. Length about $\frac{3}{4}''$.

*Calyx.*—Usually partially opened.

*Skin.*—Smooth; thin; tough; glossy; waxed. Dots — small inconspicuous; few in number, depressed. Circular distribution mostly toward calyx basin. Ground color yellow green, 23-3 (M). Color markings bright color red, 36-14 (M). General color effect bright red blush with a hint of a stripe over a variable yellow green ground color.

*Scarfskin.*—Light, confined to stem cavity when it occurs.

*Flesh.*—Juicy, color — yellowish with a green tint. Texture — fine, tender, firm crisp. Flavor — rich and subacid. Aroma — light. Quality — good.

*Core.*—Similar in structure and appearance to the standard variety Stayman, except that seed cells are usually larger and more pronounced, occasionally 6 seed cells are found instead of five.

Seeds:

*Number.*—Usually 8, not all perfect.

*Length.*—About $\frac{3}{8}''$.

*Breadth.*—About 3/16".

*Color.*—Moderate reddish brown.

Use: Market, dessert, culinary, processing.

Keeping quality: Good, about 180 days in refrigerated storage.

Insect and disease resistance: Good insect and disease resistance as determined by comparison with the effect of the usual apple insects and diseases on other apple varieties grown under the same conditions at Spring Hill, Kans.

I claim:

1. A new and distinct variety of apple tree substantially as herein shown and described characterized particularly as to novelty by the unique combination of the general resemblance to the variety Stayman apple (unpatented) but having fruit that ripens under normal conditions approximately 5–10 days ahead of the standard variety that is a brighter red color with less prominent dots borne on a tree which is smaller and more open growing with more fruiting spurs than known Stayman variety, a tendency to fruit, especially in younger trees, on one year old wood, much more waxy skin than the standard variety of Stayman apple which increases resistance to cracking and enhances shelf storage life.

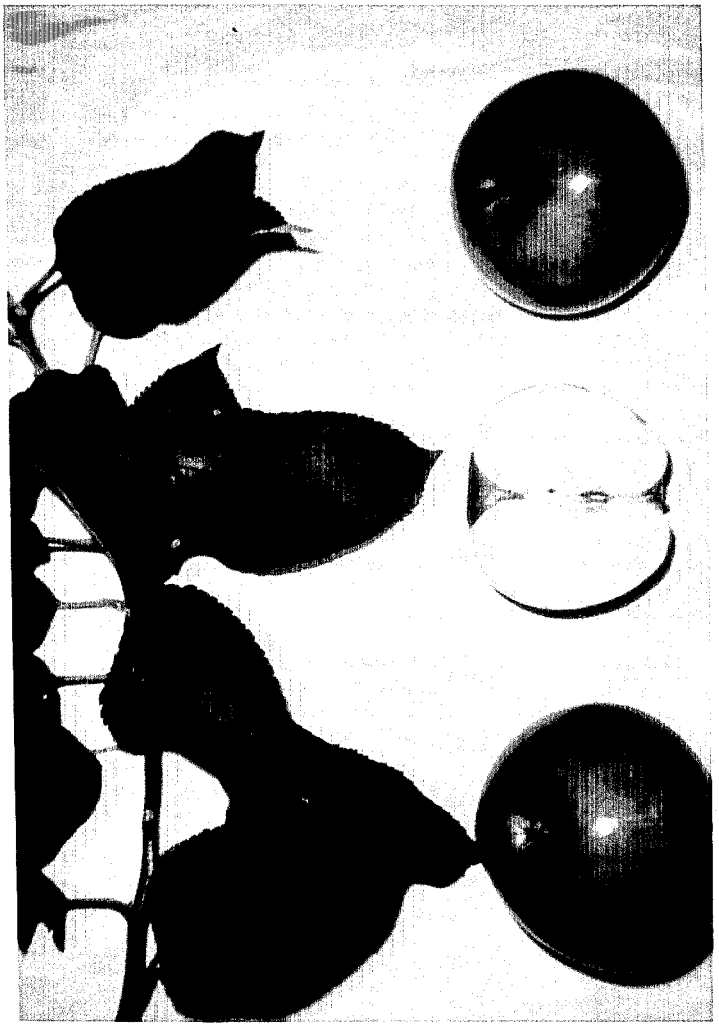

* * * * *